US006522753B1

(12) United States Patent
Matsuzawa et al.

(10) Patent No.: US 6,522,753 B1
(45) Date of Patent: Feb. 18, 2003

(54) ACTIVE NOISE CONTROL METHOD AND RECEIVER DEVICE

(75) Inventors: Hitoshi Matsuzawa, Kawasaki (JP); Yasushi Yamazaki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 09/412,291

(22) Filed: Oct. 5, 1999

(30) Foreign Application Priority Data

Oct. 7, 1998 (JP) .......................................... 10-284869

(51) Int. Cl.[7] ......................... A61F 11/06; G10K 11/16; H03B 29/00

(52) U.S. Cl. .................. 381/71.1; 381/71.8; 381/71.14; 381/123

(58) Field of Search ............................... 381/71.1, 71.6, 381/72, 71.13, 71.14, 57, 123, FOR 123, 71.2, 71.8, 71.9, 71.11, 71.12, 94.3; 379/406.01, 406.03, 406.08

(56) References Cited

U.S. PATENT DOCUMENTS 5,182,774 A * 1/1993 Bourk ........................ 379/430
5,293,578 A * 3/1994 Nagami et al. .......... 381/71.14
5,381,485 A * 1/1995 Elliott ..................... 381/71.12
5,600,729 A * 2/1997 Darlington et al. ...... 381/71.11
5,748,725 A * 5/1998 Kubo .................... 379/392.01
5,793,863 A * 8/1998 Hashimoto .................. 379/360

FOREIGN PATENT DOCUMENTS

JP 06175668 6/1994

* cited by examiner

*Primary Examiner*—Xu Mei
(74) *Attorney, Agent, or Firm*—Katten Muchin Zavis Rosenman

(57) ABSTRACT

In an active noise control method of the present invention, a noise detection signal from a noise referring microphone which detects ambient noise is inputted into noise processing units of different types to produce noise silencing signals. A selected noise silencing signal is inputted into a receiver or a speaker together with a reception signal via an adder, so that a regenerated tone from the noise silencing signal silences the ambient noise, When a nonconformance detecting unit judges that the selected noise silencing signal exceeds a predetermined range, the corresponding noise processing unit is judged to be incompatible, and a switch control unit controls a switch to select another one of the noise processing units.

15 Claims, 9 Drawing Sheets

ACTIVE NOISE CONTROL METHOD AND RECEIVER DEVICE

BACKGROUND OF THE INVENTION

1. Field of the Invention

The present invention generally relates to active noise control methods and receiver devices which detect and silence ambient noise.

Active noise control methods of silencing ambient noise by outputting a tone having a inversed phase of the absolute value of the ambient noise have been known. Such active noise control methods are applied to air ducts, for instance, to reduce indoor noise, or to handsets to facilitate communication when the ambient noise is high, 2. Description of the Related Art FIG. 1 shows a conventional active noise control method applied to a duct. A fan or an air conditioner connected to a duct 80 is a noise source 84 generating noise due to the rotation or vibration of the motor or the fan. The noise generated from the noise source 84 is transmitted through the duct 80 and released from an opening. A noise referring microphone 81 is disposed inside the duct 80 near the noise source 84 to detect noise form the noise source 84. The noise referring microphone 81 then transmits a noise signal to a noise processing unit 83.

The noise processing unit 83 turns the noise signal into a noise silencing signal having the same amplitude but an opposite phase by the combination of a filter and an amplifier, for instance. The noise silencing signal is inputted into a speaker 82 to silence the noise transmitted through the duct 80 with the tone having the opposite phase.

A microphone 85 is disposed on the opening side of the duct 80 to detect residual noise after the noise is silenced by the speaker 82, and the noise processing unit 83 is controlled to make the residual noise zero. In such a case, even if a change occurs in the sound transmission characteristics of the duct 80, the residual noise is fed back to the noise processing unit 83 to lower the noise to be released from the opening of the duct 80.

FIG. 2 Illustrates a conventional active noise control method applied to a handset. This figure shows a handset 90, a noise referring microphone 91, a receiver 92, an active noise control circuit 93, a noise processing unit 94, an adder 95, and a microphone 96. The receiver 92 of the handset 90 to be attached to the ear and the noise referring microphone 91 are situated close to each other. The microphone 96 serves as a transmitter which transmits a transmission signal corresponding to the voice. A reception signal from the other end is inputted into the receiver 92 of the handset 90 via the adder 95 to regenerate the voice.

The noise processing unit 94 comprises a filter and an amplifier, like the noise processing unit 83 shown in FIG. 1. The noise referring microphone 91 detects the ambient noise, and the noise processing unit 94 produces a noise silencing signal having the opposite phase from the ambient noise. The noise silencing signal is then inputted into the receiver to output a regenerated voice corresponding to the reception signal and a tone for silencing the ambient noise.

In such a case, the ambient noise is inputted into the noise referring microphone 91 at the same time as it enters the ear. The regenerated voice from the receiver also enters the ear and is inputted into the noise referring microphone 91. Accordingly, the regenerated voice coupled with the receiver 92 and the ambient noise are inputted into the noise referring microphone 91. The noise processing unit 94 needs to produce the noise silencing signal in accordance with the acoustic coupling condition between the receiver 92 and the noise referring microphone 91.

In the first conventional method shown in FIG. 1, to reduce the adverse influence of ambient noise, a microphone is employed to detect the ambient noise outside the handset. The phase of a noise signal from the microphone is inverted. The noise signal is then added to a transmission signal from the handset, and the noise signal and the transmission signal are added to a reception signal from the other end, thereby outputting a tone having the opposite phase from the ambient noise. This type of method is disclosed in Japanese Patent Laid-Open N. 5-110650, for instance.

In the second conventional method shown in FIG. 2, noise is detected in a plurality of positions inside a car or the like, and a tone having the opposite phase from the noise is outputted from a plurality of speakers, so that the residual noise can be minimized. The filter in a noise processing unit is controlled to obtain such an effect. This type of method is disclosed in Japanese Patent Laid-Open No. 6-175668, for instance.

Since no substantial change occurs in the sound characteristics of the duct 80 shown in FIG. 1, the active noise control by the noise processing unit 83 is relatively easy. However, if the active noise control method is applied to the handset 90 shown in FIG. 2, the acoustic space formed between the receiver 92 and the ear greatly changes during communication.

A noise signal from the noise referring microphone 91 derives from ambient noise and acoustic coupling of a regenerated voice from the receiver 92. Accordingly, the noise detection signal greatly changes due to a change of the acoustic space. Even if the noise processing unit 94 has the optimum characteristics, the ambient noise might not be efficiently silenced during communication.

If the noise processing unit 94 includes an amplifier, a loop is formed by the noise processing unit 94, the adder 95, the receiver 92, and the noise referring microphone 91. In such a case, a positive feedback condition might be caused due to the acoustic coupling characteristics between the receiver 92 and the noise referring microphone 91, resulting in reinforcement of the noise.

In the case where the phase of the noise detection signal from a microphone outside the handset is inversed and the inversed noise detection signal is added to a transmission signal and a reception signal, the entire structure cannot cope with a change in the acoustic space between the handset and the ear. As a result, the ambient noise cannot be sufficiently silenced.

In the case where a noise silencing signal to be inputted into the speaker is controlled so that the residual noise can be minimized, the amount of arithmetic operations is extremely large. It is difficult to apply this method to the handset of a telephone, especially to a potable telephone.

SUMMARY OF THE INVENTION

A general object of the present invention is to provide an active noise control method and a receiver device in which the above disadvantages are eliminated.

A more specific object of the present invention is to provide an active noise control method in which ambient noise can be silenced in a relatively simple manner.

The above objects of the present invention are achieved by an active noise control method which comprises the steps of: detecting ambient noise by a noise referring microphone; inputting the detected ambient noise into a plurality of noise processing units of different types; producing noise silencing signals by the noise processing units; selecting one of the noise silencing signals; judging whether the selected noise silencing signal exceeds a predetermined range; switching to another one of the noise processing units if the selected noise silencing signal is Nudged to be beyond the predetermined range and thus incompatible; inputting the noise silencing signal into a receiver or a speaker; and silencing the ambient noise with an output tone from the receiver or the speaker.

If the ambient noise cannot be silenced due to a circumstantial change of the ambient noise, switching from one noise silencing signal to another is automatically carried out. Thus, the ambient noise can be sufficiently silenced.

The above objects are also achieved by a receiver device comprising: a noise referring microphone which detects ambient noise and is disposed in the vicinity of a receiver or a speaker to which a reception signal is to be inputted; a plurality of noise processing units of different types into which a noise detection signal from the noise referring microphone is inputted, the noise processing units generating noise silencing signals to silence the ambient noise; a switch control unit which selects one of the noise silencing signals to be inputted into the receiver or speaker together with the reception signal; and a nonconformance detecting unit which judges the selected noise silencing signal to be beyond a predetermined range and thus incompatible, and then instructs the switch control unit to select another one of the noise silencing signals.

The above and other objects and features of the present invention will become more apparent from the following description taken in conjunction with the accompanying drawings.

DESCRIPTION OF THE PREFERRED EMBODIMENTS

Figure 1:
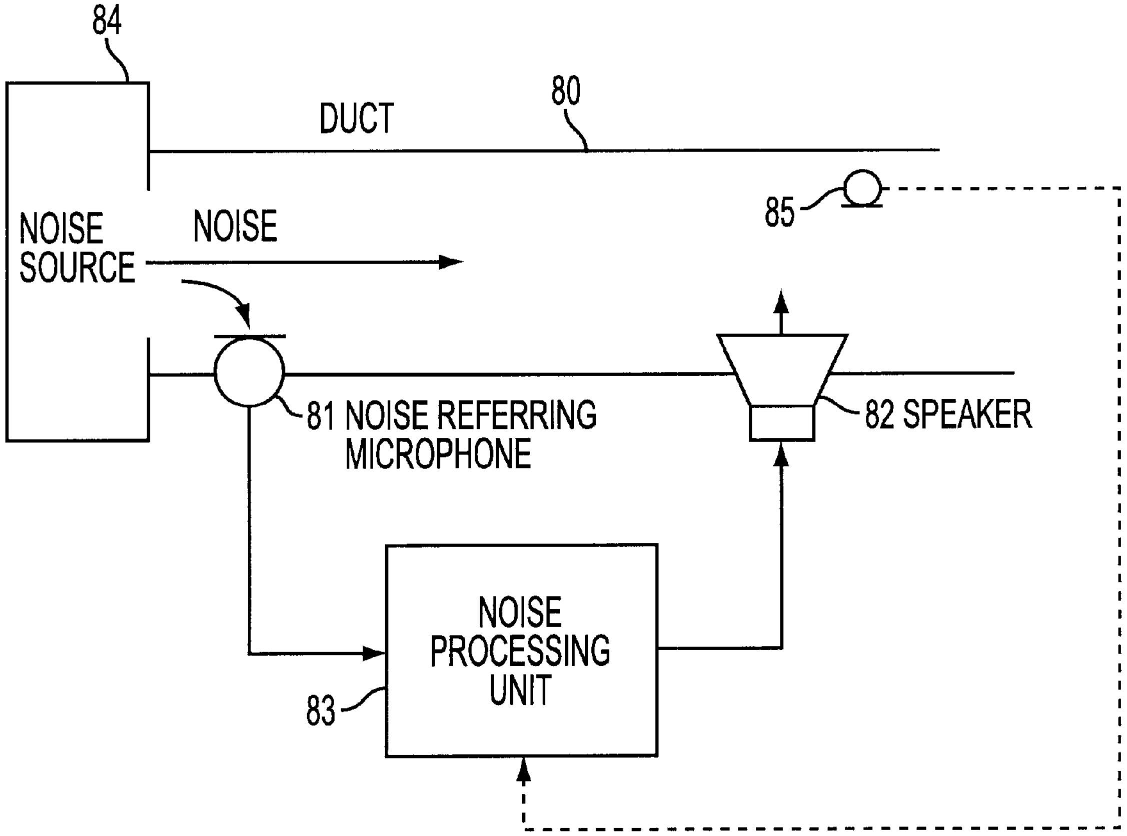
FIG. 1 (PRIOR ART)
FIG. 1 illustrates a conventional active noise control method through a duct.
Figure 2:
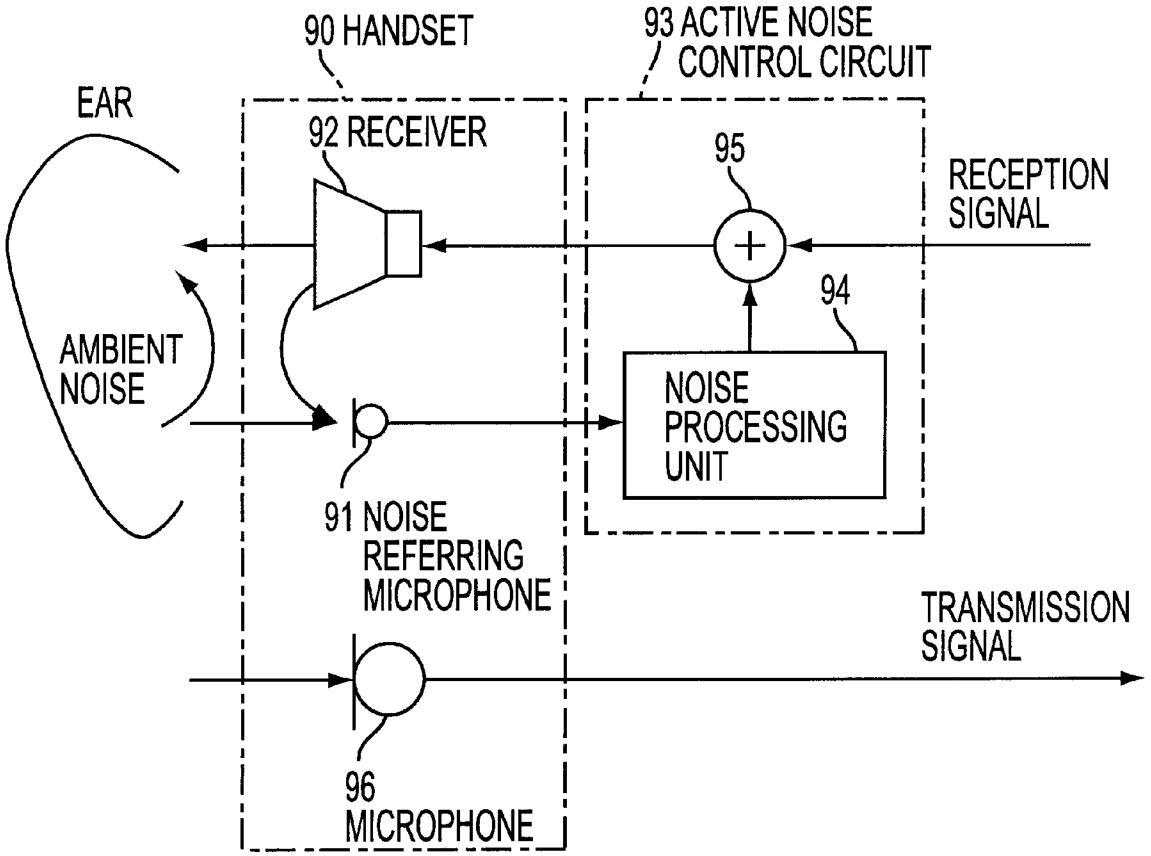
FIG. 2 (PRIOR ART)
FIG. 2 is a block diagram of the prior art.
Figure 3:
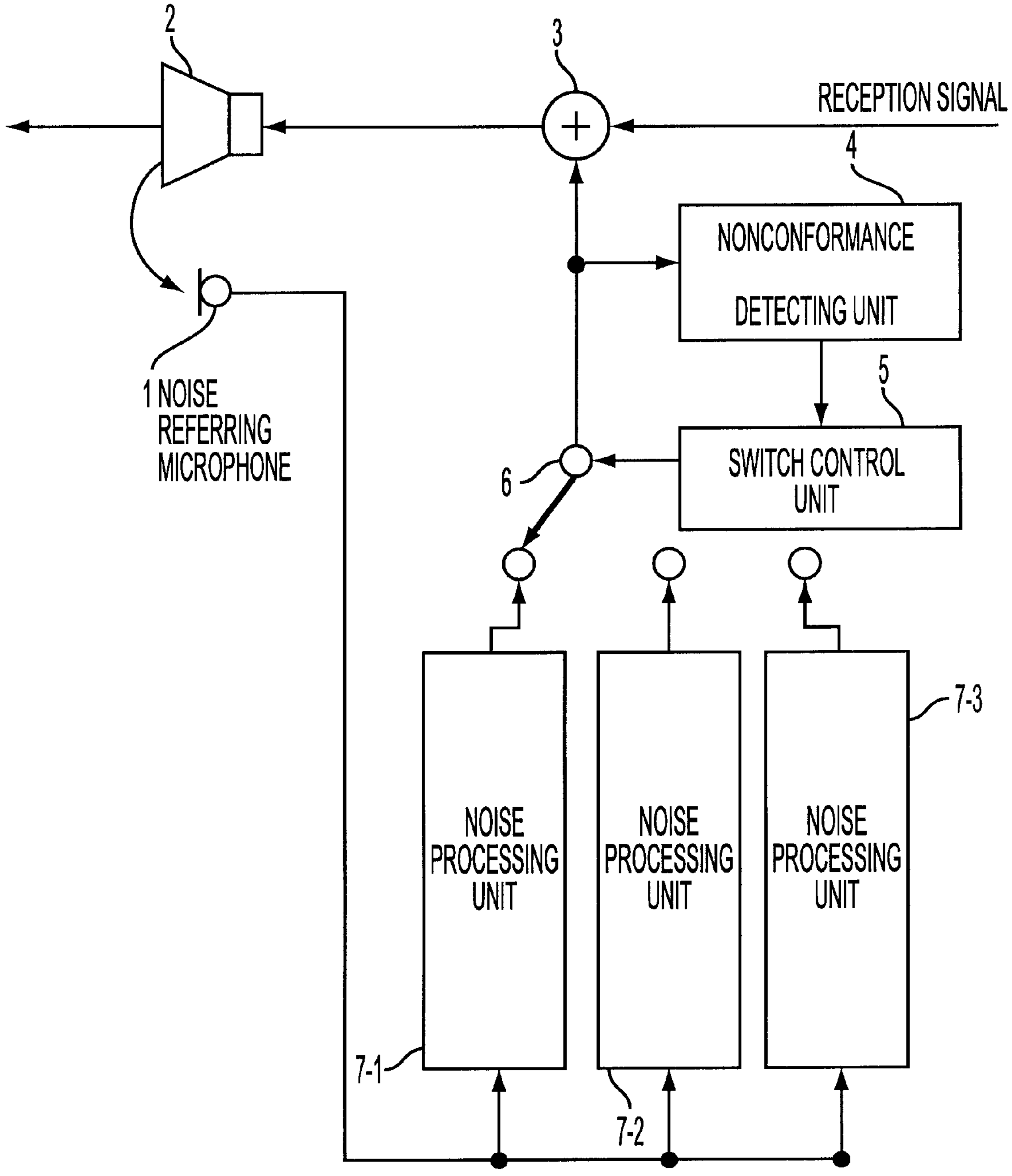
FIG. 3 is a block diagram of a first embodiment of the present invention.

FIG. 3 illustrates a first embodiment of the present invention. This embodiment comprises a noise referring microphone 1, a receiver (or a speaker) 2, an adder 3, a nonconformance detecting unit 4, a switch control unit 5, a switch 6, and noise processing units 7-1 to 7-3 including filters of different characteristics. This embodiment is applied to a receiver device such as a handset, but it may also be applied to a different type of receiver device having a speaker, instead of the receiver 2. In a case of a handset, the noise referring microphone 1 is disposed in the vicinity of the receiver 2, but in a case of a device using a speaker, the noise referring microphone 1 is disposed in a position where ambient noise can be detected.

A reception signal from a caller on the other end is inputted into the receiver (or speaker) 2 via the adder 3. A noise silencing signal from a noise processing units is then inputted into the receiver 2 via the adder 3, thereby outputting a noise silencing tone to silence the ambient noise. The nonconformance detecting unit 4 monitors the noise silencing signal inputted into the adder 3 via the switch 6. When the noise silencing signal is out of a predetermined range, the nonconformance detecting unit 4 judges that the corresponding noise processing unit is incompatible, and then transmits a switch control signal to the switch control unit 5.

For instance, the noise referring microphone 1 is disposed in the vicinity of the receiver 2 of the handset of a telephone or a portable telephone, and the noise referring microphone 1 detects the ambient noise entering the caller's ear. In such a case, a regenerated voice from the receiver 2 also enters the noise referring microphone 1 due to acoustic coupling. A noise detection signal of the noise referring microphone 1 is then inputted into the noise processing units 7-1 to 7-3. Since the noise processing units 7-1 to 7-3 have different characteristics, the noise silencing signals outputted from the respective noise processing units 7-1 to 7-3 are different from each other.

In a case where the noise silencing signal from the noise processing unit 7-1 is selected by the switch 6 and inputted into the adder 3 to silence the ambient noise by the generated voice and the noise silencing tone outputted from the receiver 2, a change might occur in the acoustic space between the receiver 2 and the ear. As a result, the noise silencing signal from the noise processing unit 7-1 might exceed the predetermined range. The nonconformance detecting unit 4 detects such a condition, and the switch control signal is transmitted to the switch control unit 5. In response to this, the switch control unit 5 controls the switch 6 to switch from the noise processing unit 7-1 to the noise processing unit 7-2, for instance.

If the noise silencing signal from the noise processing unit 7-2 is out of the predetermined range, the nonconformance detecting unit 4 detects the condition, and the switch control signal is transmitted to the switch control unit 5. The switch 6 then switches to the noise processing unit 7-3. In this manner, a compatible noise silencing signal to silence the ambient noise can be inputted into the receiver 2 by switching among the noise processing units having different characteristics. Although the three noise processing units 7-1 to 7-3 are used in this embodiment, more than three noise processing units having different characteristics may be employed.

The nonconformance detecting unit 4 judges whether each noise silencing signal exceeds the predetermined range by detecting the level or the power of each noise silencing signal. For instance, if the mean level of a noise silencing signal exceeds a predetermined level, the noise processing unit that transmitted the noise silencing signal is judged to be incompatible. If the noise processing units 7-1 to 7-3, to which the noise detection signal from the noise referring microphone 1 is inputted, are digital filters having operation functions such as DSP (Digital Signal Processor), the amount of operations is small. Thus, the entire device can be made smaller, the amount of power consumption can be reduced.

Figure 4:
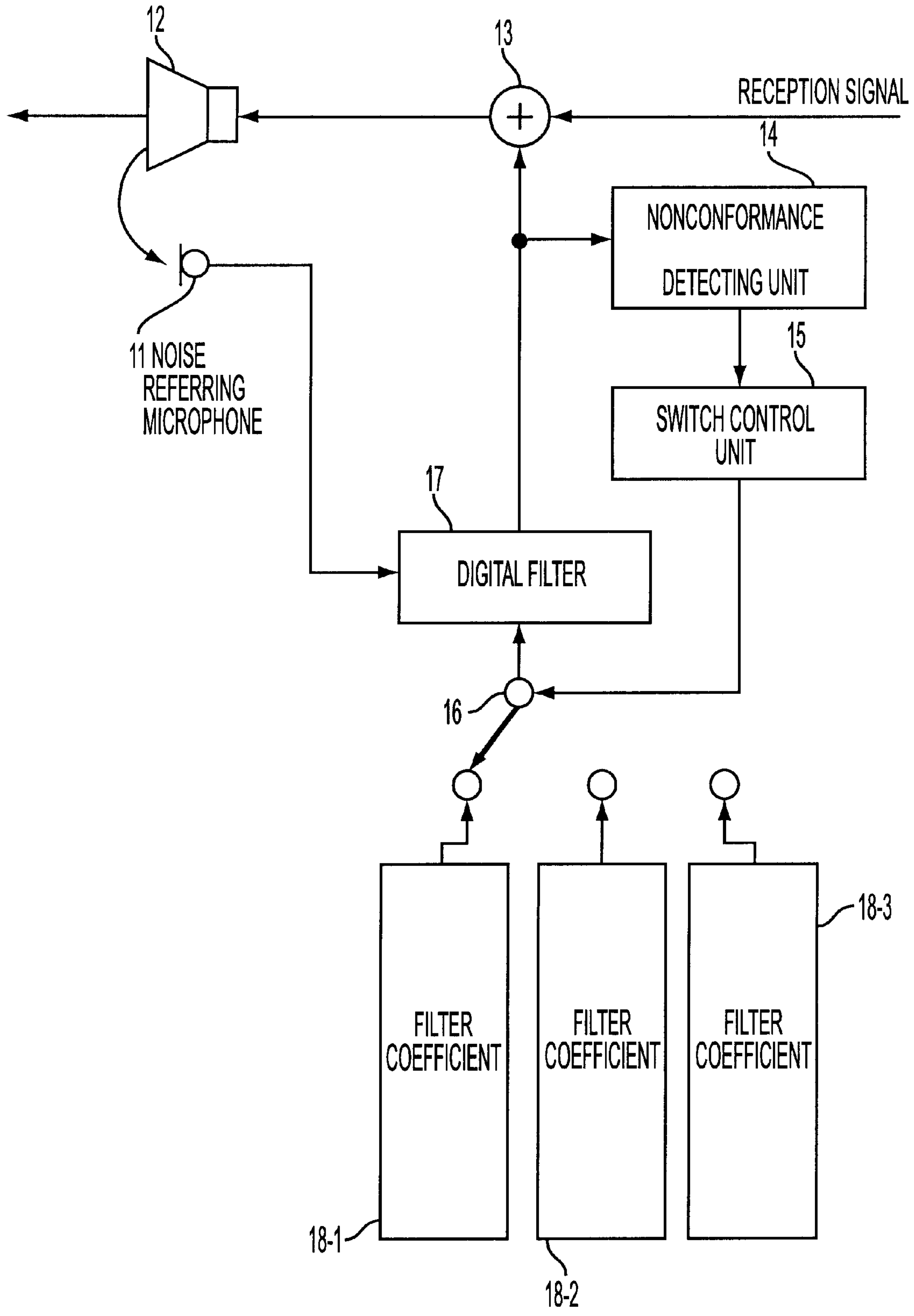
FIG. 4 is a block diagram of a second embodiment of the present invention.

FIG. 4 is a block diagram of a second embodiment of the present invention. This embodiment comprises a noise referring microphone 11, a receiver (or a speaker) 12, an adder 13, a nonconformance detecting unit 14, a switch control unit 15, a switch 16, a digital filter 17, and three different filter coefficients 18-1 to 18-3.

In this embodiment, the switch 16 switches the filter coefficient for the digital filter 17 among the filter coefficients 18-1 to 18-3, so that the same function as that of the noise processing units 7-1 to 7-3 shown in FIG. 3 can be obtained. The digital filter 17 can be a FIR (Filter Impulse Response) filter, and the coefficient for each tap can be switched by the switch 16. If the digital filter is DSP, a coefficient is prepared for each tap, and the coefficient is switched as the filter coefficient is switched in a filter operation.

Figure 5:
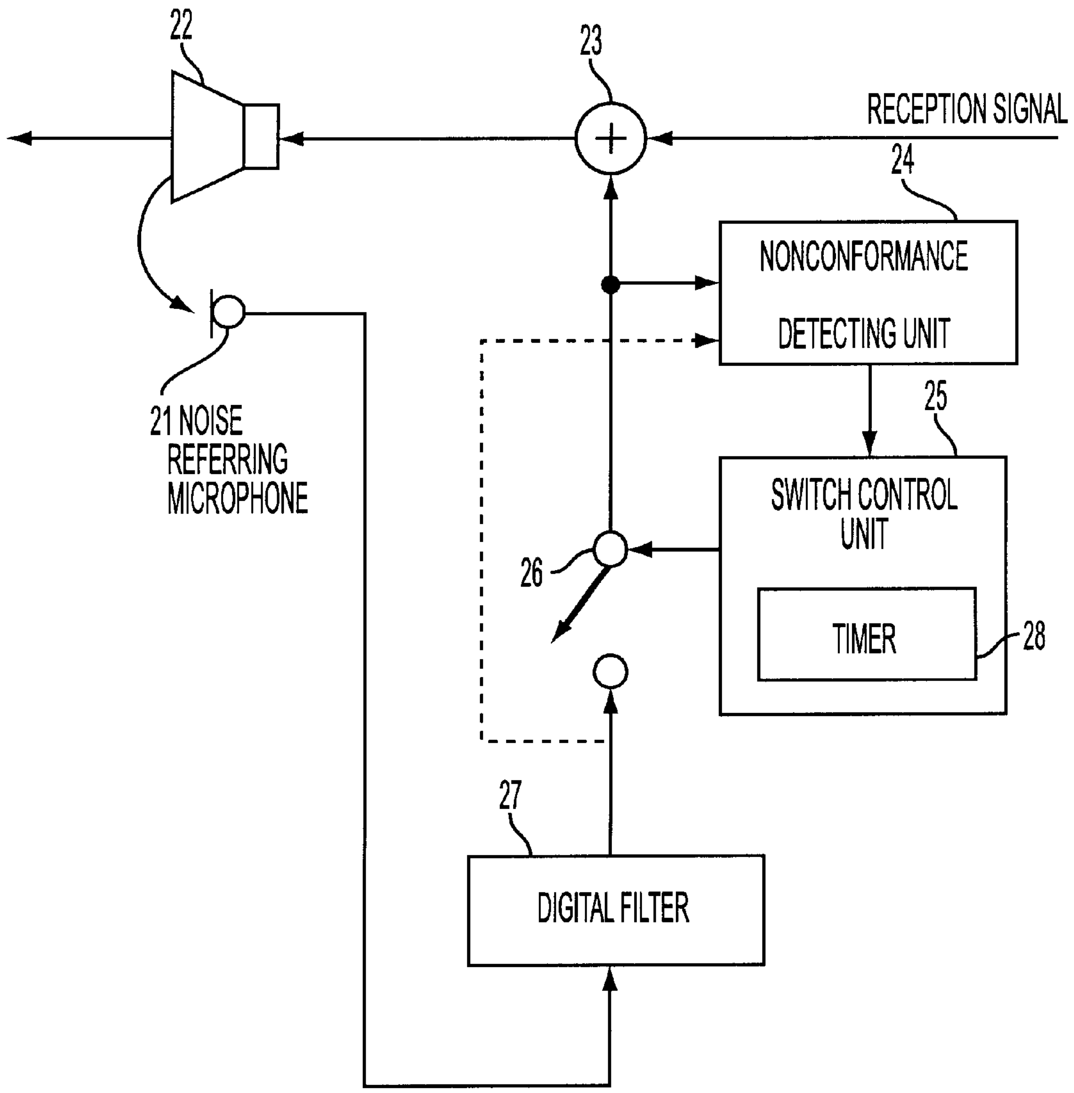
FIG. 5 is a block diagram of a third embodiment of the present invention.

FIG. 5 is a block diagram of a third embodiment of the third embodiment. This embodiment comprises a noise referring microphone 21, a receiver (a speaker) 22, an adder 23, a nonconformance detecting unit 24, a switch control unit 25, a switch 26, and a digital filter 27, and a timer 28.

In this embodiment, when the nonconformance detecting unit 24 detects that a noise silencing signal is out of the predetermined range, a switch control signal is inputted into the switch control unit 25. The switch control unit 25 then turns the switch 26 off, and starts the timer 28. Accordingly, the noise silencing signal from the digital filter 27 is not inputted into the receiver 22 via the adder 23. After a predetermined time set in the timer 28 has passed, for instance, after several seconds have passed, the switch 26 is turned on, and the noise silencing signal from the digital filter is inputted into the receiver 22 via the adder 23. In other words, the output signal from the digital filter 27 is zero during the operation of the timer 28.

As indicated by a dotted arrow in FIG. 5, the noise silencing signal from the digital filter 27 may be inputted into the nonconformance detecting unit 24. In such a case, the timer 28 can be restarted, and the switch 26 can remain off, while the noise silencing signal is out of the predetermined range.

Figure 6:
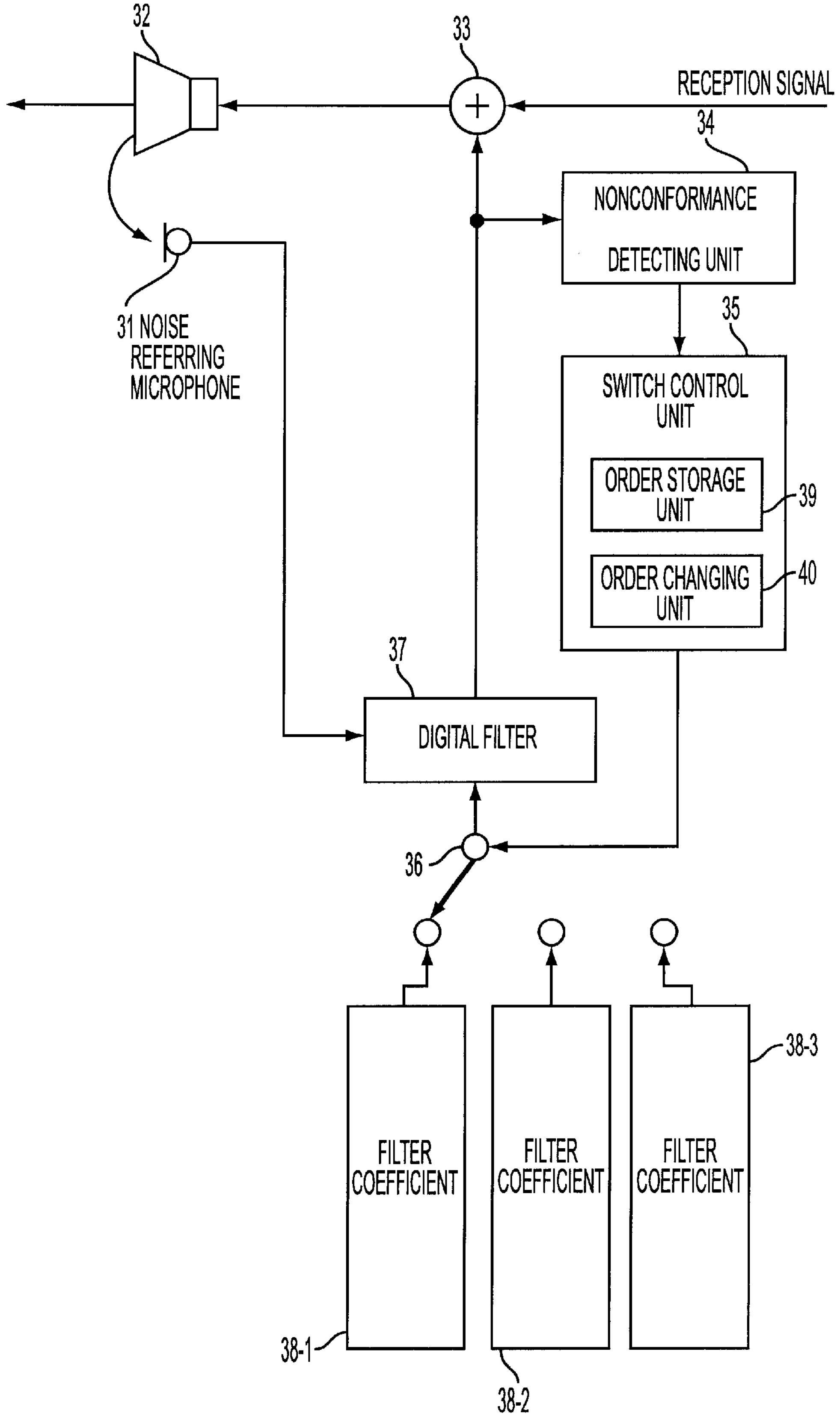
FIG. 6 is a block diagram of a fourth embodiment of the present invention.

FIG. 6 is a block diagram of a fourth embodiment of the present invention. This embodiment comprises a noise referring microphone 31, a receiver (a speaker) 32, an adder 33, a nonconformance detecting unit 34, a switch control unit 35, a switch 36, a digital filter 37, filter coefficients 38-1 to 38-3, an order storage unit 39, and an order changing unit 40.

This embodiment is similar to the second embodiment, except that the order storage unit 39 stores the switching order of the filter coefficients 38-1 to 38-3 when the noise silencing signal exceeds the predetermined range, so that the switch control unit 35 can control the switch 36 to switch among the filter coefficients 38-1 to 38-3 in accordance with the stored sequence. Accordingly, when the nonconformance detecting unit 34 Judges that the noise silencing signal exceeds the predetermined range, the filter coefficients 38-1 to 38-3 are switched in the sequential order to select a compatible filter coefficient.

The order changing unit 40 changes the switching order stored in the order storage unit 39. For instance, the switching order is controlled so that the filter coefficient that have been selected for the longest period of time among the filter coefficients 38-1 to 38-3 can have a higher priority next time the filter coefficients are switched. With this order changing unit 40, a more compatible filter coefficient can be promptly selected, compared with a case where a filter coefficient is selected in the fixed switching order stored in the order storage unit 39.

Figure 7:
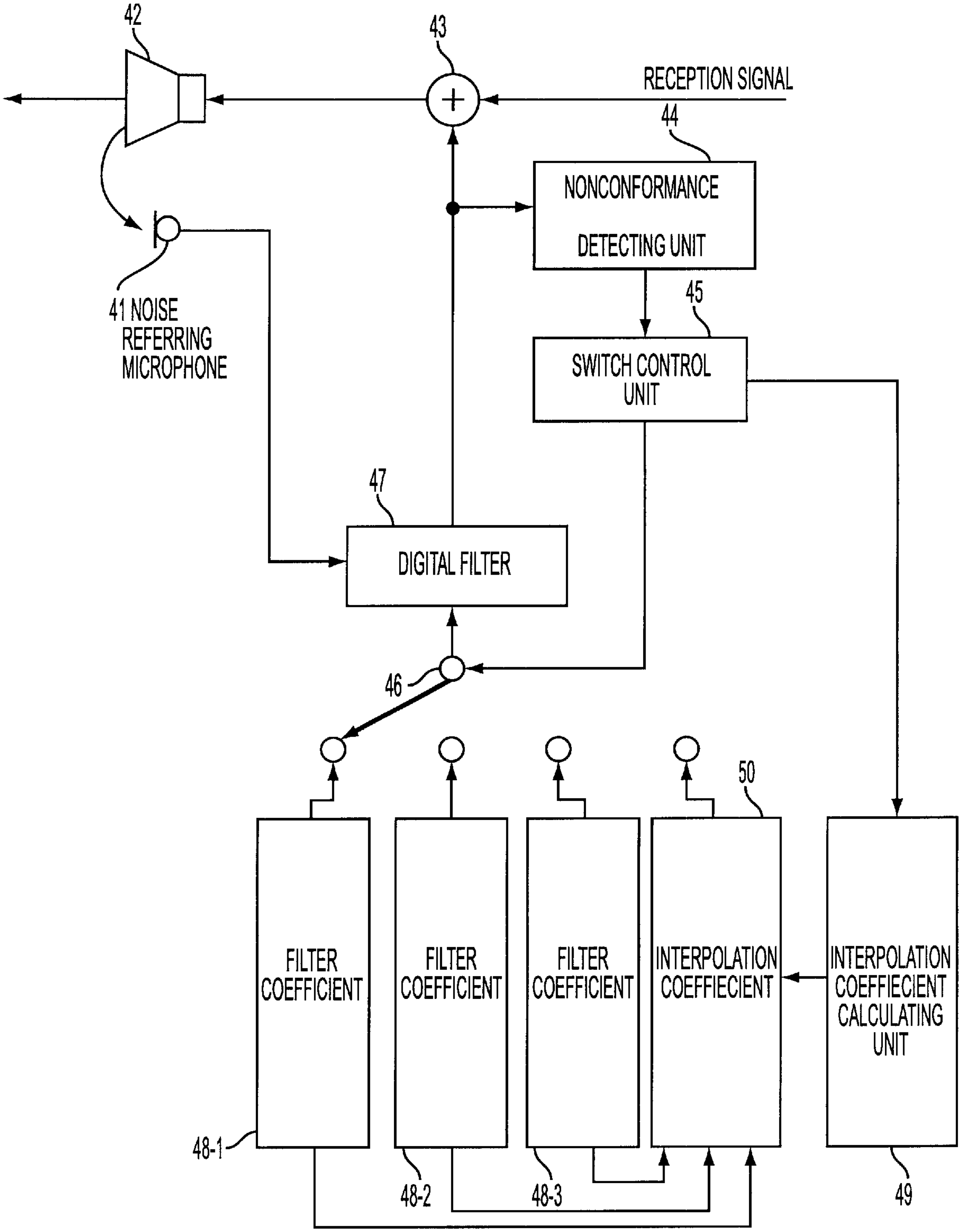
FIG. 7 is a block diagram of a fifth embodiment of the present invention.

FIG. 7 is a block diagram of a fifth embodiment of the present invention. This embodiment comprises a noise referring microphone 41, a receiver (speaker) 42, an adder 43, a nonconformance detecting unit 44, a switch control unit 45, a switch 46, a digital filter 47, filter coefficients 48-1 to 48-3, an interpolation coefficient calculating unit 49, an interpolation coefficient 50.

In this embodiment, when the nonconformance detecting unit 44 judges the noise silencing signal from the digital filter 47 to be beyond the predetermined range and thus incompatible, the filter coefficients 46-1 to 48-3 are interpolated when the switch control unit 45 controls the switching of the filter coefficients. The interpolation coefficient calculating unit 49 obtains the interpolation coefficient 50 based on the selection information from the switch control unit 45 that has selected from the filter coefficients 48-1 to 48-3. The switch control unit 45 then controls the switch 46 to temporarily select the interpolation coefficient 50.

In a case where the noise silencing signal from the filter coefficient 48-1 is beyond the predetermined range and judged to be incompatible, for instance, the interpolation coefficient 50 is obtained based on the filter coefficients 48-1 and 48-2, and the switch 46 switches from the filter coefficient 48-1 to the interpolation coefficient 50. The noise silencing signal from the digital filter according to the interpolation coefficient 50 is inputted into the receiver 42 via the adder 43, and the switch 46 then switches to the filter coefficient 48-2.

In a case where the jth filter coefficient of a filter i is para_i[j], the jth filter coefficient of the filter k is para_k[j], and the jth interpolation coefficient of the mth sample from the start of interpolation from the filter i to the filter k is para_i_k_m[j], the operation in the linear interpolation using M samples is expressed as:

$$\text{para\_i\_k\_m}[j] = \{\text{para\_k}[j] \times m + \text{para\_i}[j] \times (M - m)\} / M$$

By this interpolation, the filter coefficient gradually changes from the filter coefficient of the filter i to the filter coefficient of the filter k. Accordingly, no sudden change occurs in the noise silencing signals, and an unnatural change of the silencing tone of the ambient noise can be avoided.

Figure 8:
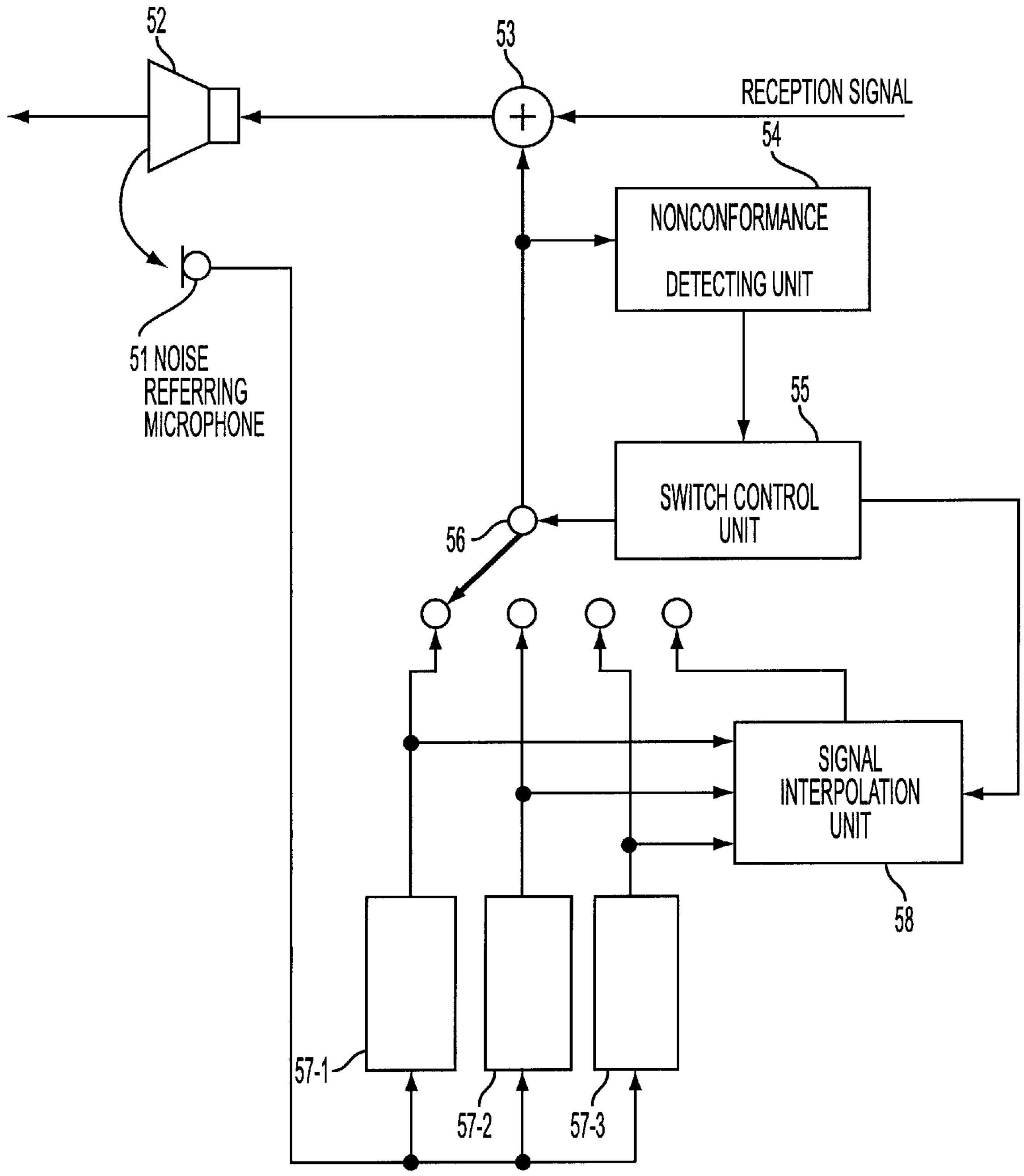
FIG. 8 is a block diagram of a sixth embodiment of the present invention.

FIG. 8 is a block diagram of a sixth embodiment of the present invention. This embodiment comprises a noise referring microphone 51, a receiver (speaker) 52, an adder 53, a nonconformance detecting unit 54, a switch control unit 55, a switch 56, filters 57-1 to 57-3, and a signal interpolation unit 58.

In this embodiment, a noise silencing signal from the filters 57-1 to 57-3 of different types corresponding to noise processing units of different types is inputted into the signal interpolation unit 58. Based on a switch control signal from the switch control unit 55 performs interpolation using the noise silencing signal from the selected filter and a noise silencing signal from a next selected filter when the noise silencing signal from selected filter is Judged to be incompatible. The switch control unit 55 controls the switch 56 to temporarily select the signal interpolation unit 58 during the switching process.

In a case where a noise silencing signal calculated with a filter i is sig_i[m], the noise silencing signal calculted with the filter k is sig_k[m], and the interpolation noise silencing signal of the mth sample from the start of interpolation from the filter i to the filter k is sig_i_k[m], the operation in the linear interpolation using M samples is expressed as:

$$sig\_i\_k[m] = \{sig\_k[m] \times m + sig\_i[m] \times (M - m)\}/M$$

Accordingly, when the switch 56 switches among the filters 57-1 to 57-3, the noise silencing signal interpolated by the signal interpolation unit 58 is inputted into the receiver 52 via the adder 53. Thus, as in the case where the filter coefficients are interpolated, no sudden change occurs in the noise silencing signals, and a sudden unnatural change of the silencing tone of the ambient noise can be avoided.

Figure 9A:
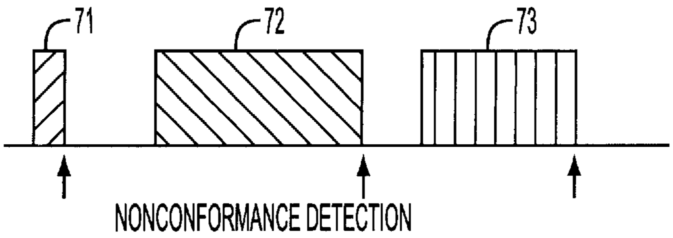
FIGS. 9A to 9G illustrate operations of the embodiments of the present invention.

FIGS. 9A to 9G shows operations of the embodiments of the present invention. In these figures, arrows indicate the timing for nonconformance detection. FIG. 9A shows a case where the filter coefficients are switched in order of numerals 71, 72, 73, . . . when a noise silencing signal is judged to be beyond the predetermined range and thus incompatible, and there are inactive periods during which the noise silencing signals are zero.

In such a case, the switching order is stored in the order storage unit 39 shown in FIG. 6, so that the filter coefficient switching can be performed at every nonconformance detection. When the filter coefficient switching comes full circle, the filter coefficient switching in the switching order stored in the order storage unit 39 is repeated. With the inactive periods, a sudden change of the noise silencing signals can be avoided at the time of switching the filter coefficients, so that adverse influence on a regenerated voice from the receiver (or the speaker) can be prevented.

Figure 9B:
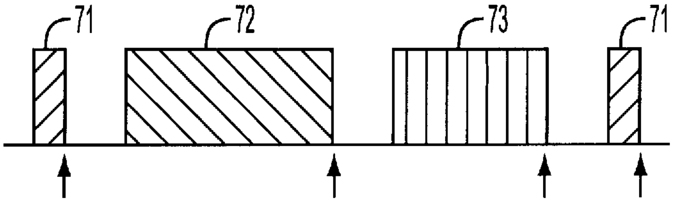
Figure 9C:
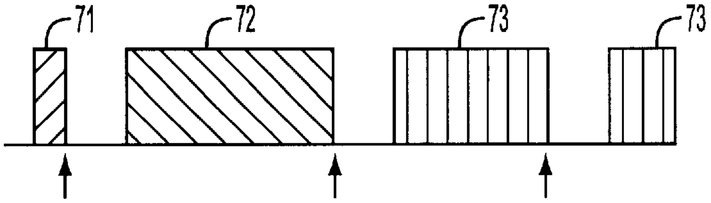

FIG. 9B shows a case where the filter coefficient switching is performed in a predetermined switching order. Since the filter coefficient 72 is selected for a long period of time, the ambient noise can be effectively silenced using the noise silencing signal produced with the filter coefficient 72. FIG. 9C shows a case where a filter coefficient which has been selected recently and judged to be compatible has priority of selection over the other filter coefficients when nonconformance is detected after the switching of the filter coefficients has come full circle. In such a case, the order changing unit 40 shown in FIG. 6 changes the switching order stored in the order storage unit 39.

Figure 9D:
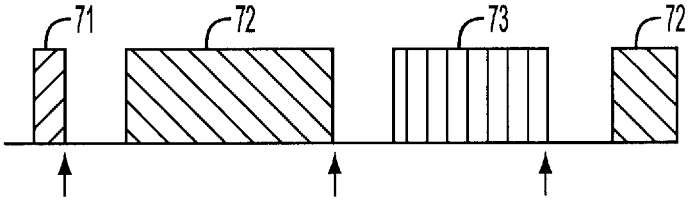

FIG. 9D shows a case where a filter coefficient which has been compatible for the longest period of time has priority of selection over the other filter coefficients when nonconformance is detected after the switching of the filter coefficients has come full circle. For instance, if the filter coefficient 72 has been selected for the longest period of time and the filter coefficient 73 has been selected for the second longest period of time, the filter coefficient 72 is selected at first nonconformance detection, and the filter 73 is selected at the next nonconformance detection, as shown in FIG. 9D. In this manner, a more compatible filter coefficient can be promptly selected, compared with the case where each filter coefficient is selected in order. The switch control unit 35 shown in FIG. 6 controls the switch 6 and monitors each period of selecting each filter coefficient. The periods of selecting the filter coefficient are then compared with each other, so that the order changing unit 40 can change the switching order stored in the order storage unit 39.

Figure 9E:
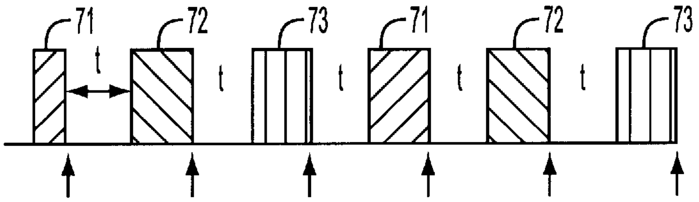
Figure 9F:
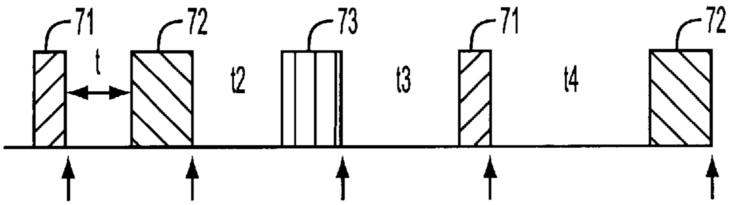

FIG. 9E shows a case where all the inactive periods t are uniform. FIG. 9F shows a case where the inactive periods are varied as t1, t2. t3, . . . . For instance, the switching of the filter coefficients can be performed in order with uniform inactive intervals, and after one cycle, the switching of the filter coefficients can be performed with longer inactive intervals. If nonconformance is detected in a short period of time with any filter coefficient, the ambient noise is in an unpredictable condition. Therefore, the inactive periods, during which the noise silencing signal is zero, are prolonged, and the active noise control is then resumed.

Figure 9G:
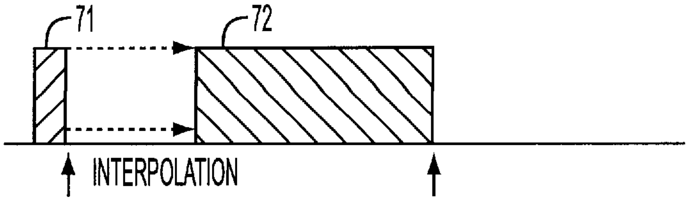

FIG. 9G shows a case where an interpolation process is carried out when the filter coefficient is switched from the filter coefficient 71 to the filter coefficient 72. For instance, the interpolation coefficient calculating unit 49 shown in FIG. 7 obtains the interpolation coefficient 50 from the filter coefficients 71 and 72. This interpolation coefficient 50 is selected during an inactive period of the switching of the filter coefficients, and a noise silencing signal is produced in the meantime. In such a case, the filter coefficients of the digital filter are switched in the order of the filter coefficient 71→the interpolation coefficient 50→the filter coefficient 72. Thus, no sudden change occurs in the noise silencing signal, and the ambient noise can be smoothly silenced.

Also, a noise silencing signal obtained by interpolating a noise silencing signal from the filter coefficient 71 and a noise silencing signal from the filter coefficient 72 can be used. As in the case where the interpolation coefficient is employed, no sudden change occurs in the noise silencing signals, and the ambient noise can be smoothly silenced. For instance, the signal interpolation unit 58 shown in FIG. 8 is employed to interpolate the noise silencing signals. Also, in a case where no interpolation process is carried out to switch the filter coefficients at the inactive intervals, the rising of the noise silencing signals can be made more gradual.

The present invention is not limited to the specifically disclosed embodiments, but variations and modifications may be made without departing from the scope of the present invention.

The present application is based on Japanese priority application No. 10-284869, filed on Oct. 7, 1998, the entire contents of which are hereby incorporated by reference.

What is claimed is:

1. An active noise control method comprising the steps of:

detecting ambient noise by a noise referring microphone;

inputting the detected ambient noise into a plurality of noise processing units of different types;

producing noise silencing signals by the noise processing units;

selecting one of the noise silencing signals;

judging whether the selected noise silencing signal exceeds a predetermined range;

switching to another one of the noise processing units if the selected noise silencing signal is judged to be beyond the predetermined range and thus incompatible;

inputting the noise silencing signal into a receiver or a speaker; and silencing the ambient noise with all output tone from the receiver or the speaker.

2. The active noise control method as claimed in claim 1, wherein;

the plurality noise processing units of different types are digital filters to switch different filter coefficients; and the filter coefficients are switched when the selected noise silencing signal is judged to be beyond the predetermined range and thus incompatible.

3. The active noise control method as claimed in claim 2, further comprising the step of switching to a next filter coefficient after temporarily switching to an interpolation coefficient which interpolates a current filter coefficient and the next filter coefficient at the time of switching the filter coefficients.

4. The active noise control method as claimed in claim 1, further comprising the step of switching to a next noise silencing signal of a next noise processing unit after temporarily switching to an interpolation signal obtained by interpolating a noise silencing signal of a current noise processing unit and the noise silencing signal of the next noise processing unit at the time of switching the noise processing units.

5. The active noise control method as claimed in claim 1, wherein the switching of the noise processing units is performed in a predetermined order.

6. The active noise control method as claimed in claim 1, wherein the switching of the noise processing units is performed in an order that gives priority to a noise processing unit which has been compatible recently.

7. The active noise control method as claimed in claim 1, wherein the switching of the noise processing units is performed in an order that gives priority to a noise processing unit which has been compatible for the longest period of time among all the noise processing units.

8. The active noise control method as claimed in claim 1, wherein the switching of the noise processing units includes inactive periods in which the noise silencing signal temporarily becomes zero.

9. The active noise control method as claimed in claim 8, wherein the inactive periods are changed in accordance with past conformance conditions.

10. A receiver device comprising:

a noise referring microphone which detects ambient noise and is disposed in the vicinity of a receiver or a speaker to which a reception signal is to be inputted;

a plurality of noise processing units of different types into which a noise detection signal from the noise referring microphone is inputted, said noise processing units generating noise silencing signals to silence the ambient noise;

a switch control unit which selects one of the noise silencing signals to be inputted into the receiver or speaker together with the reception signal; and a nonconformance detecting unit which judges the selected noise silencing signal to be beyond a predetermined range and thus incompatible, and then instructs the switch control unit to select another one of the noise silencing signals.

11. The receiving device as claimed in claim 10, wherein the noise processing units are digital filters which switches filter coefficients of different types.

12. The receiver device as claimed in claim 10, wherein the switch control unit comprises an order storage unit which stores a switching order of the noise processing units when the nonconformance detecting unit detects nonconformance.

13. The receiver device as claimed in claim 10, wherein the switch control unit comprises:

an order storage unit which stores a switching order of the noise processing units; and an order changing unit which changes the switching order in accordance with past conformance conditions.

14. The receiver device as claimed in claim 11, further comprising an interpolation coefficient calculating unit which outputs an interpolation coefficient for interpolating filter coefficients of the digital filters upon switching the filter coefficients based on switching information form the switch control unit, wherein the switch control unit temporarily selects the interpolation coefficient from the interpolation coefficient calculating unit, and then switches to a next filter coefficient.

15. The receiver device as claimed in claim 10, further comprising a signal interpolation unit which outputs an interpolation signal for interpolating noise silencing signals upon switching noise silencing signals, wherein the switch control unit temporarily selects the interpolation signal from the signal interpolation unit, and switches to a next noise silencing signal.

* * * * *